US011013437B2

(12) United States Patent
Kinser et al.

(10) Patent No.: US 11,013,437 B2
(45) Date of Patent: May 25, 2021

(54) NANOPATTERNED BIOSENSOR ELECTRODE FOR ENHANCED SENSOR SIGNAL AND SENSITIVITY

(71) Applicants: International Business Machines Corporation, Armonk, NY (US); Yale University, New Haven, CT (US)

(72) Inventors: Emily R. Kinser, Poughkeepsie, NY (US); Themistoclis Kyriakides, Branford, CT (US); Jagannath Padmanabhan, New Haven, CT (US)

(73) Assignees: International Business Machines Corporation, Armonk, NY (US); YALE UNIVERSITY, New Haven, CT (US)

(*) Notice: Subject to any disclaimer, the term of this patent is extended or adjusted under 35 U.S.C. 154(b) by 90 days.

(21) Appl. No.: 16/245,942

(22) Filed: Jan. 11, 2019

(65) Prior Publication Data

US 2019/0142310 A1 May 16, 2019

Related U.S. Application Data

(62) Division of application No. 15/005,690, filed on Jan. 25, 2016, now Pat. No. 10,213,144.

(51) Int. Cl.
*G01N 27/32* (2006.01)
*C22C 1/10* (2006.01)
(Continued)

(52) U.S. Cl.
CPC .......... *A61B 5/1486* (2013.01); *A61B 5/1468* (2013.01); *A61B 5/14532* (2013.01);
(Continued)

(58) Field of Classification Search
None
See application file for complete search history.

(56) References Cited

U.S. PATENT DOCUMENTS

| 2,933,458 A | 4/1960 | King et al. |
| 6,136,630 A | 10/2000 | Weigold et al. |

(Continued)

FOREIGN PATENT DOCUMENTS

| CN | 1598694 A | 3/2005 |
| CN | 106094426 A | 11/2016 |
| KR | 1020160092635 A | 8/2016 |

OTHER PUBLICATIONS

Padmanabhan, J., et al., "Engineering Cellular Response Using Nanopatterned Bulk Metallic Glass", American Chemical Society Nano, Apr. 2014, pp. 4366-4375, vol. 8, No. 5.
(Continued)

*Primary Examiner* — George Wyszomierski
(74) *Attorney, Agent, or Firm* — Scully, Scott, Murphy & Presser, P.C.; Steven J. Meyers

(57) ABSTRACT

An electrode structure, which can be used as a biosensor, is provided that has non-random topography located on one surface of an electrode base substrate. The non-random topography of the electrode structure and the electrode base substrate of the electrode structure are of unitary construction and unitary composition and thus there is no interface is located between these elements of the electrode structure.

19 Claims, 4 Drawing Sheets

(51) Int. Cl.
*A61B 5/1486* (2006.01)
*A61B 5/145* (2006.01)
*G01N 27/327* (2006.01)
*A61B 5/1468* (2006.01)
*B82Y 40/00* (2011.01)
*B82Y 15/00* (2011.01)

(52) U.S. Cl.
CPC ..... *G01N 27/3271* (2013.01); *G01N 27/3278* (2013.01); *A61B 2562/0209* (2013.01); *A61B 2562/0285* (2013.01); *A61B 2562/046* (2013.01); *A61B 2562/125* (2013.01); *B82Y 15/00* (2013.01); *B82Y 40/00* (2013.01)

(56) References Cited

U.S. PATENT DOCUMENTS

| | | | |
|---|---|---|---|
| 6,359,444 | B1 | 3/2002 | Grimes |
| D469,540 | S | 1/2003 | Holker et al. |
| 6,914,279 | B2 | 7/2005 | Lu et al. |
| 7,005,048 | B1 | 2/2006 | Watanabe et al. |
| 7,294,910 | B2 | 11/2007 | Thomas et al. |
| 7,524,408 | B2 | 4/2009 | Monbouquette et al. |
| 7,604,592 | B2 | 10/2009 | Freeman et al. |
| 7,627,938 | B2 | 12/2009 | Kim et al. |
| 7,894,914 | B2 | 2/2011 | Stahmann et al. |
| 7,949,382 | B2 | 5/2011 | Jina |
| 7,955,483 | B2 | 6/2011 | Gu et al. |
| 8,076,125 | B2 | 12/2011 | McGimpsey |
| 8,097,926 | B2 | 1/2012 | De Graff et al. |
| 8,221,822 | B2 | 7/2012 | Flanagan et al. |
| 8,303,800 | B2 | 11/2012 | Fukuda et al. |
| 8,485,245 | B1* | 7/2013 | Prest ............... B22D 11/01 164/463 |
| 8,529,835 | B2 | 9/2013 | Kaplan et al. |
| 8,668,978 | B2 | 3/2014 | Malima et al. |
| 8,741,380 | B2 | 6/2014 | Yoshida et al. |
| 8,772,228 | B2 | 7/2014 | Stupp et al. |
| 8,808,516 | B2 | 8/2014 | Melosh et al. |
| 8,907,384 | B2 | 12/2014 | Pace et al. |
| 9,958,441 | B2 | 5/2018 | Zhang et al. |
| 2005/0269285 | A1 | 12/2005 | Jung et al. |
| 2007/0148653 | A1 | 6/2007 | Yoshida |
| 2009/0137423 | A1 | 5/2009 | Higson |
| 2009/0155800 | A1 | 6/2009 | Hong et al. |
| 2009/0243584 | A1 | 10/2009 | Zhang et al. |
| 2009/0272285 | A1 | 11/2009 | Kraus et al. |
| 2010/0006451 | A1 | 1/2010 | Gordon et al. |
| 2010/0066346 | A1 | 3/2010 | Zhang et al. |
| 2010/0310773 | A1 | 12/2010 | Yoshida et al. |
| 2010/0318193 | A1 | 12/2010 | Desai et al. |
| 2011/0027458 | A1 | 2/2011 | Boock et al. |
| 2011/0073475 | A1 | 3/2011 | Kastanos et al. |
| 2011/0091510 | A1 | 4/2011 | Lele et al. |
| 2011/0230735 | A1 | 9/2011 | Wolfe et al. |
| 2011/0233063 | A1 | 9/2011 | Seki et al. |
| 2011/0301716 | A1 | 12/2011 | Sirivisoot et al. |
| 2011/0319734 | A1 | 12/2011 | Gottlieb et al. |
| 2012/0218550 | A1 | 8/2012 | O'Mahony |
| 2012/0312061 | A1* | 12/2012 | Pham ............... C22C 1/002 72/60 |
| 2013/0025814 | A1* | 1/2013 | Demetriou ......... C22F 1/00 164/250.1 |
| 2013/0079608 | A1 | 3/2013 | Miller et al. |
| 2013/0112321 | A1* | 5/2013 | Poole ............... B21K 23/00 148/241 |
| 2013/0150822 | A1 | 6/2013 | Ross |
| 2014/0230854 | A1 | 8/2014 | Lopez et al. |
| 2014/0238574 | A1 | 8/2014 | Kinser |
| 2016/0331290 | A1 | 11/2016 | Oh et al. |
| 2017/0025453 | A1 | 1/2017 | Bornfreund et al. |
| 2017/0202079 | A1 | 7/2017 | Norton et al. |
| 2017/0209079 | A1 | 7/2017 | Kinser et al. |
| 2017/0241003 | A1* | 8/2017 | Na .................... C22C 45/003 |
| 2018/0020957 | A1 | 1/2018 | Kinser |
| 2018/0217080 | A1 | 8/2018 | Kinser |
| 2018/0252662 | A1 | 9/2018 | Kinser |
| 2019/0056343 | A1 | 2/2019 | Kinser |
| 2019/0142310 | A1 | 5/2019 | Kinser et al. |
| 2020/0077956 | A1 | 3/2020 | Kinser |

OTHER PUBLICATIONS

Kaushik, N., et al., "Metallic glass thin films for potential biomedical applications", Journal of Biomedical Materials Research B: Applied Biomaterials, Oct. 2014, pp. 1544-1552, vol. 1028, issue 7.
"Gold! The crystal structure of success", Downloaded from https://crystallography365.wordpress.com/2014/01/17/gold-the-crystal-structure-of-success/ Posted Jan. 17, 2014, 4 pages.
Lee et al., "Nanostructured indium-tin-oxide films fabricated by all-solution processing for functional transparent electrodes", Optics Express, Oct. 24, 2011, pp. 21803-21808, vol. 19, No. 22.
Mailoa, et a., "Textured conducting glass by nanosphere lithography for increased light absorption in thin-film solar cells", Journal of Physics D: Applied Physics, published Feb. 3, 2014, 9 pages.
List of IBM Patents or Patent Applications Treated as Related dated Jan. 11, 2019, 2 pages.
Zhai, D. et al., "Highly Sensitive Glucose Sensor Based on Pt Nanoparticle/Polyaniline Hydrogel Heterostructures", ACS Nano, Mar. 2013, pp. 3540-3546, vol. 7, No. 4.
S.-H. Parng, et al. "Effect of temperature and glucose concentration on a glass-based sensor for long-term stability investigation", J. Micro/Nanolith. MEMS MOEMS, Jan.-Mar. 2011, pp. 013003-1 to 013003-5, vol. 10(1).
J. Gajdzik, et al., "Enzyme immobilisation on self-organised nanopatterned electrode surfaces", Phys. Chem. Chem. Phys., Sep. 2010, pp. 12604-12607, 12.
G. Freckmann, et al., "System Accuracy Evaluation of 27 Blood Glucose Monitoring Systems According to DIN EN ISO 15197", Diabetes Technology & Therapeutics, Feb. 12, 2010, pp. 221-231, vol. 12, No. 3.
M. Cardosi, et al., "Amperometric Glucose Sensors for Whole Blood Measurement Based on Dehydrogenase Enzymes", Intech, Dehydrogenases, Chapter 13, Published: Nov. 14, 2012, pp. 319-354.
D. C. Deshpande, et al., "Development of a nanoscale heterostructured glucose sensor using modified rnicrofabrication processes", J. Micro/Nanolith., Apr.-Jun. 2008, MEMS MOEMS, pp. 023005-1 to 023005-6, vol. 7(2).
Browne, D. J., et al., "Comparison of nucleation and growth mechanisms in alloy solidification to those in metallic glass crystallisation—relevance to modeling", Transactions of The Indian Institute of Metals, Aug.-Oct. 2009, pp. 406-412, vol. 62, Issues 4-5.
Pitt, E.B., et al., "Temperature dependence of the thermoplastic formability in bulk metallic glasses", Journal of Applied Physics published online Aug. 23, 2011, pp. 043518-1 to 043518-7, 110.
International Search Report dated May 14, 2018 received in a related foreign application.
Carmo, M., et al., "Bulk Metallic Glass Nanowire Architecture for Electrochemical Applications", American Chemical Society, Published online Mar. 3, 2011, pp. 2979-2983, vol. 5, No. 4.
Office Action dated Apr. 6, 2018 received in parent U.S. Appl. No. 15/005,690.
Office Action dated Jul. 23, 2020 received in U.S. Appl. No. 16/169,654.

* cited by examiner

NANOPATTERNED BIOSENSOR ELECTRODE FOR ENHANCED SENSOR SIGNAL AND SENSITIVITY

BACKGROUND

The present application relates to an electrode structure and a method of forming the same. More particularly, the present application relates to a nanopatterned electrode structure of uniform construction and uniform composition that can be used for biosensing applications.

Biosensors with enhanced signal and sensitivity are essential to provide reliable data for both medical and environmental monitoring. Such biosensors are especially needed for areas related to food and water supply security as well as the healthcare industry. For healthcare, glucose sensors comprise a significant portion of the existing biosensor market. Platinum (Pt) is commonly used as a working electrode in glucose sensors, and platinum has demonstrated biocompatibility. External electrochemical sensors (so-called "Test-Strips") are commonly used. However, limitations exist on the accuracy and applicability of test strip sensors.

In vivo glucose sensors, which are implanted into a human body, can be used to continuously monitor blood sugar. However, the foreign body response restricts in vivo biosensors. Moreover, the foreign body response can reduce the sensor signal output over time.

Despite advances made in biosensor technology, there is still a need to provide low-cost biosensors that exhibit enhanced sensor signal and sensitivity, and which may also mitigate the foreign body response.

SUMMARY

An electrode structure, which can be used as a biosensor, is provided which has non-random topography located on one surface of an electrode base. Improved sensor signal and sensitivity can be obtained in such an electrode structure if there is no interface between the non-random topography of the electrode structure and the electrode base of the electrode structure. By "no interface" is it meant that the non-random topography and the electrode base are of unitary construction (i.e., one piece) and unitary composition (i.e., a same material).

In one aspect of the present application, an electrode structure is provided that can be used as a biosensor. In one embodiment of the present application, the electrode structure of the present application includes an electrode base having non-random topography located on one surface of the electrode base. In accordance with the present application, the electrode base and the non-random topography are of uniform construction and uniform composition.

In another aspect of the present application, a method of forming an electrode structure is provided that includes providing a mold having a pattern that comprises both an electrode base shape and a nanotopography shape. An amorphous metal, which may also be referred to as a "metallic glass" or a "bulk metallic glass," is then introduced into the mold by utilizing a thermoplastic forming process to provide an electrode structure comprising the amorphous metal (i.e., metallic glass) and having the electrode base substrate shape and the nanotopography shape resulting from the influence of the mold. The mold is then removed from the electrode structure, and a biological functionalization material is then added to the electrode structure.

DETAILED DESCRIPTION

Figure 1:
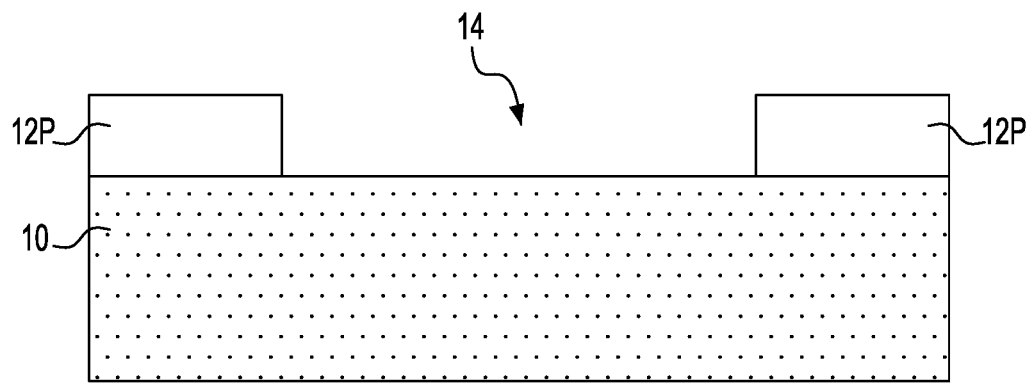
FIG. 1 is a cross sectional view of an exemplary structure including a first mask layer patterned to have an opening for defining an electrode base shape and located on a surface of a substrate in accordance with an embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Referring first to FIG. 1, there is illustrated an exemplary structure including a first mask layer 12P patterned to have an opening 14 for defining an electrode base shape and located on a surface of a substrate 10 in accordance with an embodiment of the present application. That is, the opening 14 has a shape that is used in the present application for defining the electrode base of a resultant electrode structure to be subsequently formed. The shape of opening 14 may also include any corresponding wiring for the electrode structure. In one embodiment, first mask layer 12P may be comprised of a photosensitive material such as a photoresist. In an alternate embodiment, first mask layer 12P may be comprised of dielectric film, hereafter referred to as a hardmask, which has been patterned using photolithography or other means known to those skilled in the art.

The substrate 10 that can be employed in the present application includes any material that can be readily patterned as described herein and that can be subsequently removed from the resultant electrode structure that is formed within a mold made from substrate 10.

In one embodiment of the present application, the substrate 10 is composed of a semiconductor material. The term "semiconductor material" denotes a material that has an electrical conductivity value between a conductor, such as copper, and an insulator, such as glass. Semiconductor materials may exist as elemental materials or compound materials. Examples of semiconductor materials that may be used as substrate 10 include Si, SiGe, SiGeC, SiC, Ge alloys, III/V compound semiconductors or II/VI compound semiconductors. In some embodiments of the present application, the substrate 10 may comprise a single semiconductor material. In other embodiments of the present application, the substrate 10 may comprise a multilayered stack of semiconductor materials.

In one embodiment of the present application, the semiconductor material that can provide substrate 10 may be a single crystalline semiconductor material such as, for example, single crystalline silicon. By "single crystalline" it is meant a material in which the crystal lattice of the entire sample is continuous and unbroken to the edges of the sample, with no grain boundaries. In another embodiment of the present application, the semiconductor material that can provide substrate 10 may be a polycrystalline semiconductor material such as, for example, polycrystalline silicon. By "polycrystalline" it is meant a material that is composed of many crystallites (i.e., grains) of varying sizes and orientation. In yet a further embodiment of the present application, the semiconductor material that can provide substrate 10 may be an amorphous semiconductor material such as, for example, amorphous silicon. By "amorphous" it is meant a material that lacks a long-range crystal order of a crystal.

In some embodiments of the present application, the semiconductor material that provides substrate 10 is a bulk semiconductor material. By "bulk" it is meant that the entirety of the substrate 10 is composed of at least one semiconductor material.

Another material that may be used as substrate 10 is a dielectric material. By "dielectric material" it is meant a material (i.e., insulator) that does not conduct electricity readily. In one embodiment of the present application, the dielectric material that can provide substrate 10 is comprised of a semiconductor oxide such as, for example, silicon dioxide. In another embodiment of the present application, the dielectric material that can provide substrate 10 may be composed of a semiconductor nitride such as, for example, silicon nitride. Other dielectric materials such as, for example, dielectric metal oxides, including aluminum oxide, may also be used as the material which comprises substrate 10.

In some embodiments, substrate 10 may comprise a combination of a semiconductor material and a dielectric material. For example, substrate 10 may be a material stack of, from bottom to top, a silicon dioxide layer and a silicon layer. An optional handle substrate can be located beneath the silicon dioxide layer. The optional handle substrate may be comprised of a semiconductor material, insulator, or conductive material.

Substrate 10 may also be composed of a ceramic material, an elemental metal, an alloy of an elemental material or any other material or combination of materials that can be readily patterned as described herein and thereafter readily removed from an electrode structure that is subsequently formed into a mold made from the material that provides substrate 10.

The first mask layer 12P that can be used in the present application may include a positive-tone photoresist material, a negative-tone photoresist material, a hybrid photoresist material, or a hardmask layer comprised of a dielectric material. The first mask layer 12P can be provided by first depositing a blanket layer of photoresist material on a surface of substrate 10. Following deposition of the blanket layer of photoresist material, the blanket layer of photoresist material is patterned to have an opening 14 that defines an electrode base shape. When a hardmask layer is utilized, a blanket layer of a hardmask material (such as, silicon nitride) is first deposited and thereafter a patterned photoresist containing an opening that defines the electrode base shape is formed atop the blanket layer of hardmask material. The pattern in the patterned photoresist is then transferred to the blanket hardmask material as an intermediate step, followed by subsequent transfer of the pattern to the substrate 10. The transferring of the pattern may include one or more etching steps. The patterned photoresist can be removed from atop the hardmask material anytime after the pattern has been transferred to the blanket layer of hardmask material.

The opening 14 defining the electrode base shape is not limited to any specific shape. In one embodiment of the present application, the opening 14 (and thus the electrode base shape) is a polygonal. In such an embodiment, the opening 14 (and thus the electrode base shape) may be triangular, quadrilateral or pentagonal. In other embodiments, the opening 14 (and thus the electrode base shape) may be circular or elliptical. The opening 14 may also include additional structures such as wiring or probe pads required to read out the electrical signal from the final electrode structure (not shown), thus resulting in a compound shape for opening 14.

Figure 2:
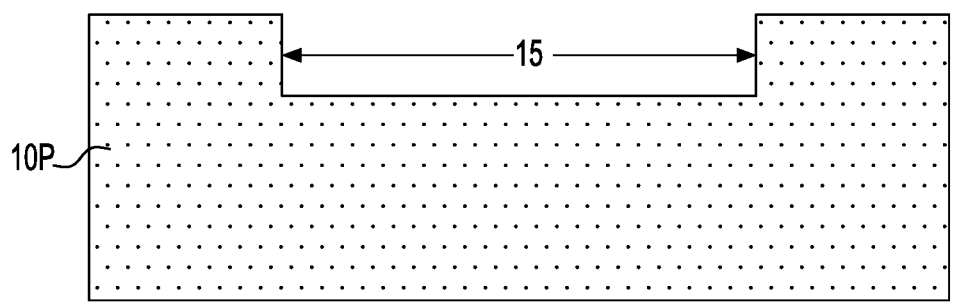
FIG. 2 is a cross sectional view of the exemplary structure of FIG. 1 after transferring the electrode base shape into the substrate to provide a patterned substrate having the electrode base shape and removing the first mask layer from the resultant structure.

Referring now to FIG. 2, there is illustrated the exemplary structure of FIG. 1 after transferring the electrode base shape into the substrate 10 to provide a patterned substrate 10P having the electrode base shape 15 and removing the first mask layer 14P from the resultant substrate structure. As is shown, the electrode base shape 15 does not extend through the entirety of the substrate 10. Instead, some portion of substrate 10 remains beneath the electrode base shape 15 after the pattern transfer process.

The transferring of the electrode base shape 15 defined by opening 14 into the substrate 10 may be performed utilizing one or more etching processes. Examples of etching processes that may be used in the present application to transfer the electrode base substrate shape 15 into the substrate 10 may include dry etching, wet etching or any combination thereof. Dry etching may include one of reactive ion etching (RIE), ion beam etching, plasma etching, or laser ablation. Wet etching may include a chemical etchant that is selective in removing the material that provides the substrate 10 relative to the mask layer material. The first mask layer 12P can be removed from the patterned substrate 10P utilizing any conventional resist stripping process such as, for example, oxygen ashing or other chemical means. In some embodiments, a planarization process may be used to remove the first mask layer 12P.

Figure 3:
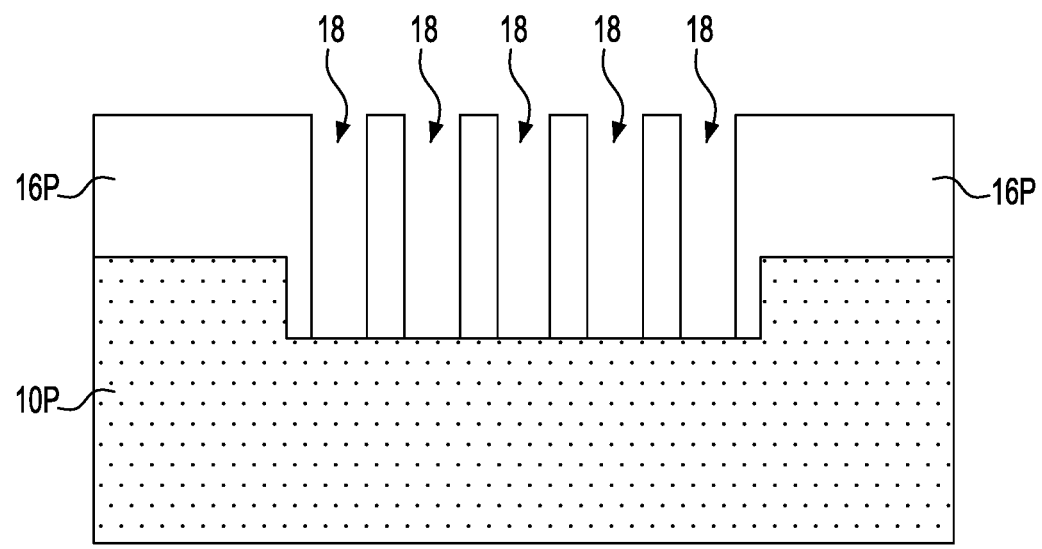
FIG. 3 is a cross sectional view of the exemplary structure of FIG. 2 after forming a second mask layer patterned to have a plurality of openings that collectively define a nanotopography shape on the patterned substrate.

Referring now to FIG. 3, there is illustrated the exemplary structure of FIG. 2 after forming a second mask layer 16P patterned to have a plurality of openings 18 that collectively define a nanotopography shape on the patterned substrate 10P. By "nanotopography shape" is meant an array of non-random (i.e., regular repeating) individual articulated features whose size is less than the size of the electrode base substrate shape 15 provided into substrate 10.

The plurality of openings 18 may have various shapes and sizes. For example, the plurality of openings 18 may have a shape of a circle, an ellipse, or an annular structure. In one embodiment of the present application, the plurality of openings 18 that is provided may have a critical dimension, i.e., diameter or width, from 5 nm to 900 nm. In another embodiment of the present application, the plurality of openings 18 that is provided may have a critical dimension from 20 nm to 300 nm.

In one embodiment of the present application, each opening of the plurality of openings 18 has a pitch ratio of from 2:1 to 100:1. By "pitch" it is meant the center-to-center distance of nearest-neighbor features. The "pitch ratio" is defined based upon the critical dimension of the feature, where the spacing between the features is proportional to the critical dimension of the features. In another embodiment of the present application, each opening of the plurality of openings 18 has a pitch ratio of from 2:1 to 20:1.

In one embodiment of the present application, the second mask layer 16P is a photoresist material that can be formed and patterned as defined above. In another embodiment, the second mask layer 16P is a dielectric layer which can be patterned as defined above. In yet another embodiment of the present application, the second mask layer 16P is a component of a block copolymer such as, for example, a self-assembling block copolymer. Notably, some block copolymers can be processed to include an ordered pattern containing repeating structural units. In one embodiment, the block copolymer may contain any numbers of the polymeric block components A and B arranged in any manner. For example, the block copolymer layer can have either a linear or a branched structure. In one embodiment, the block copolymer is a linear diblock copolymer having the formula of A-B. Specific examples of suitable block copolymers that can be used for forming the structural units may include, but are not limited to: polystyrene-block-polymethylmethacrylate (PS-b-PMMA), polystyrene-block-polyisoprene (PS-b-PI), polystyrene-block-polybutadiene (PS-b-PBD), polystyrene-block-polyvinylpyridine (PS-b-PVP), polystyrene-block-polyethyleneoxide (PS-b-PEO), polystyrene-block-polyethylene (PS-b-PE), polystyrene-b-polyorganosilicate (PS-b-POS), polystyrene-block-polyferrocenyldimethylsilane (PS-b-PFS), polyethyleneoxide-block-polyisoprene (PEO-b-PI), polyethyleneoxide-block-polybutadiene (PEO-b-PBD), polyethyleneoxide-block-polymethylmethacrylate (PEO-b-PMMA), polyethyleneoxide-block-polyethylethylene (PEO-b-PEE), polybutadiene-block-polyvinylpyridine (PBD-b-PVP), and polyisoprene-block-polymethylmethacrylate (PI-b-PMMA).

In order to form the ordered pattern containing repeating structural units, the block copolymer is first dissolved in a suitable solvent system to form a block copolymer solution, which is then applied onto a surface to form a block copolymer layer, followed by annealing of the block copolymer layer, thereby effectuating phase separation between different polymeric block components, i.e., first and second units contained in the block copolymer. The segregated block copolymer layer can then be exposed, and developed to provide the second mask layer 16P having the plurality of openings 18.

Figure 4:
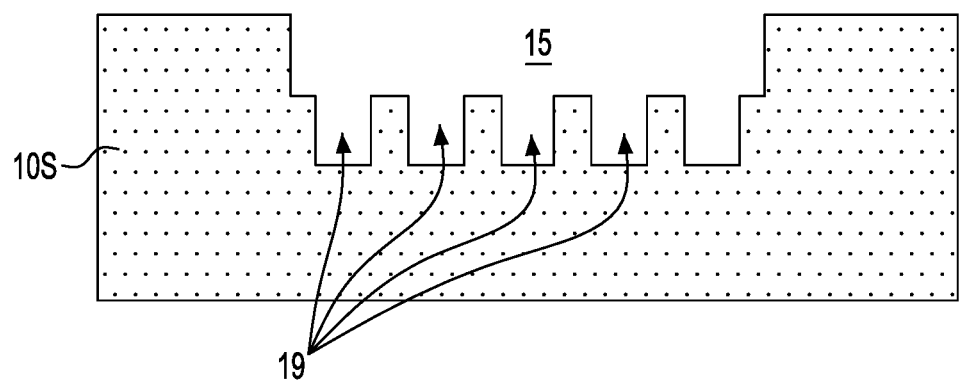
FIG. 4 is a cross sectional view of the exemplary structure of FIG. 3 after transferring the nanotopography shape into the patterned substrate to provide a mold containing the electrode base substrate shape and the nanotopography shape and removing the second mask layer.

Referring now to FIG. 4, there is illustrated the exemplary structure of FIG. 3 after transferring the nanotopography shape providing by the plurality of openings 18 into the patterned substrate 10P to provide a mold 10S containing the electrode base shape 15 and the nanotopography shape 19 and removing the second mask layer 16P. As stated above, the nanotopography shape that is transferred into the patterned substrate 10P includes an array of non-random (i.e., regular repeating) individual articulated features (each non-random individual articulated feature is labeled as element 19 in FIG. 4) whose critical dimension is less than the size of the electrode base shape 15 provided into substrate 10.

As is shown in FIG. 4, the nanotopography shape including each non-random individual articulated feature 19 is formed within the area including the electrode base shape 15. As is also shown, the nanotopography shape including each non-random individual articulated feature 19 may not extend through the entirety of the mold 10S. Instead, some portion of the mold 10S may remain beneath each non-random individual articulated feature 19 that collectively define the nanotopography shape after the pattern transfer process. In another embodiment (not shown), the nanotopography shape may extend entirely through the thickness of mold 10S.

Each non-random individual articulated feature 19 that is formed utilizing the second mask layer 16P has a shape, width, and pitch defined by the plurality of openings 18 and the etching process used to transfer the pattern of openings 18 to substrate 10P. For example, each non-random individual articulated feature 19 may have a shape of a rod, a cone, an ellipse, or an annular structure. In one embodiment of the present application, each non-random individual articulated feature 19 may have a critical dimension ranging in size from 5 nm to 900 nm. In another embodiment of the present application, each non-random individual articulated feature 19 may have a critical dimension ranging in size from 20 nm to 300 nm.

In one embodiment of the present application, each non-random individual articulated feature 19 has a pitch ratio of from 2:1 to 100:1. In another embodiment of the present application, each non-random individual articulated feature 19 has a pitch ratio of from 2:1 to 20:1.

In one embodiment of the present application, each non-random individual articulated feature 19 has a height from 5 nm to 300 µm. In another embodiment of the present application, each non-random individual articulated feature 19 has a height from 50 nm to 20 µm.

In one embodiment of the present application, each non-random individual articulated feature 19 has an aspect ratio (i.e., ratio of width to height) of 1:1 to 500:1. In another embodiment of the present application, each non-random individual articulated feature 19 has an aspect ratio (i.e., width to height) of 2:1 to 100:1.

The height and aspect ratio of each non-random individual articulated feature 19 is determined by the depth at which each non-random individual articulated feature 19 is formed into the patterned substrate 10P.

The transferring of the nanotopography shape into the patterned substrate 10P can be achieved utilizing one of the etching processes mentioned above for transferring the electrode base shape into substrate 10. In one embodiment of the present application, and when second mask layer 16P is composed of a photoresist material, the second mask layer 16P can be removed utilizing a conventional resist developer such as, for example, ashing. In another of the present application, and when the second mask layer 16P is a component of a block copolymer or a dielectric layer, second mask layer 16P can be removed utilizing an etchant that is selective in removing the component of the block copolymer or dielectric layer.

Figure 5:
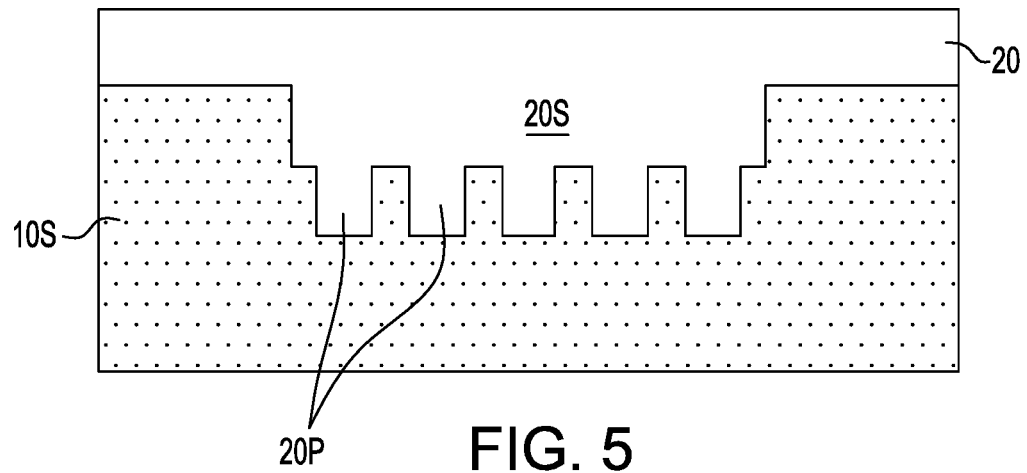
FIG. 5 is a cross sectional view of the exemplary structure of FIG. 4 after introducing a fill material, such as metallic glass, into the mold to provide an electrode structure comprising the fill material and having the electrode base shape and the nanotopography shape of the mold.

Referring now to FIG. 5, there is illustrated the exemplary structure of FIG. 4 after introducing a fill material 20 into the mold 10S to provide an electrode structure having the electrode base shape and the nanotopography shape of the mold 10S. The fill material 20 may consist of any conductive material which may be deposited into the openings for the electrode base shape 15 and nanotopography shapes 19 formed in mold 10S. The fill material 20 may include a metallic material, including an alloy of more than one metal. The fill material 20 may consist of an alloy which is comprised of both metallic and non-metallic components. Fill material 20 may be comprised of alloy with one component being selected from platinum, copper, silver, gold, tungsten, aluminum, iron, palladium, nickel, titanium, zirconium, phosphorus, or carbon. In one embodiment, the fill material 20 may be in a crystalline state; in an additional embodiment, fill material 20 may exist in an amorphous state. In yet another embodiment, fill material 20 may be a metallic glass.

When fill material 20 is introduced in the electrode base shape 15, the resulting structure provides an electrode base 20S of the electrode structure, while the nanotopography shape 19 provides non-random topography in the form of repeating individually articulated features 20P of the electrode structure. In accordance with the present application, the electrode base substrate 20S of the electrode structure, and the non-random topography provided by the repeating individually articulated features 20P are of unitary construction (i.e., single piece) and of a same composition (i.e., metallic glass). Thus, the electrode structure (20S, 20P) that is provided lacks an interface between the electron base substrate 20S and the non-random topography provided by the repeating individually articulated features 20P.

Each repeating individually articulated feature 20P that is provided has a shape, width, pitch, height and aspect ratio as defined above for each non-random individual articulated feature 19.

In an embodiment of the present application in which fill material 20 consists of a metallic glass, the metallic glass fill material is introduced into mold 10S utilizing a thermoplastic forming process to provide the electrode structure (20S, 20P) of the present application. The thermoplastic forming process includes first providing a piece of metallic glass. By "metallic glass" it is meant a solid metallic material, usually an alloy, with a disordered amorphous atomic structure. Metallic glasses can also be referred to herein as amorphous metals or glassy metals. In the case where fill material 20 is a metallic glass in the present application, the fill material is non-crystalline or amorphous. Moreover, the fill material 20 that is used in the present application is an electrically conductive material. The fill material 20 that can be employed may include an element selected from platinum, copper, nickel, phosphorous, palladium, zirconium, silver, aluminum, carbon or alloy or alloys thereof. In one example, the fill material 20 that can be utilized in the present application includes a platinum-based bulk metallic glass alloy such as, but not limited to, a PtCuNiP alloy. The piece of metallic glass may be any shape and may have a size that is greater than the volume of the electrode base shape 15 of mold 10S.

Once the piece of metallic glass is placed atop the mold 10S shown in FIG. 4, the metallic glass fill material may be heated above the glass transition temperature, $T_g$, of the metallic glass, and external compressive force may be applied to both the fill material 20 and the mold 10S (not shown), which is referred to as "thermoplastic forming." The thermoplastic forming process may be performed under an inert ambient such as, for example, helium, argon, neon or mixtures thereof. In other embodiments, the thermoplastic forming process may be performed under vacuum or in air.

In one embodiment, a continuous load may be applied to the mold 10S. In another embodiment, incremental loads may be applied to the mold 10S. Upon application of compressive force above the glass transition temperature, the metallic glass begins to flow and enter into mold 10S, partially or totally filling both the electrode base structure and the nanotopography. During the application of compressive force and flow of metallic glass, the metallic glass remains amorphous.

Upon completion of the thermoplastic forming process, the compressive force may be released and the resultant structure shown in FIG. 5 including mold 10S and the nanopatterned electrode structure (20S, 20P) can be cooled to room temperature, with the result that fill material 20 may conform to the shape of mold 10S.

Figure 6:
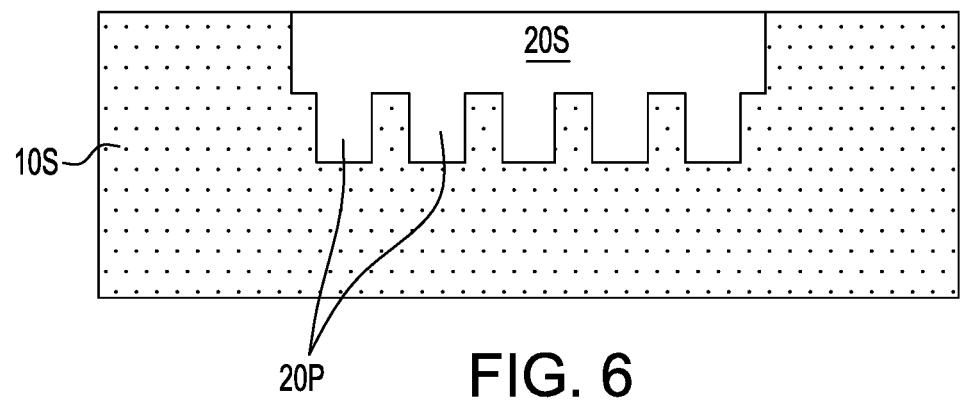
FIG. 6 is a cross sectional view of the exemplary structure of FIG. 5 after removing excess fill material that may be located above the electrode base substrate shape of the mold.

Referring now to FIG. 6, there is illustrated the exemplary structure of FIG. 5 after removing excess fill material 20 that is located above the electrode base shape 15 of the mold 10S. After the excess fill material 20 is removed, the resultant electrode structure (20S, 20P) has a planar surface that is opposite the surface that includes the non-random topography in the form of repeatable non-random individually articulated features 20P.

In one embodiment of the present application, the removal of the excess fill material 20 may be performed by a planarization process such as, for example, chemical mechanical planarization and/or grinding. In another embodiment of the present application, the removal of the excess fill material may be performed by utilizing a chemical etch back process; in still another embodiment, the excess fill material may be removed using a reactive ion etch (RIE) process.

Figure 7:
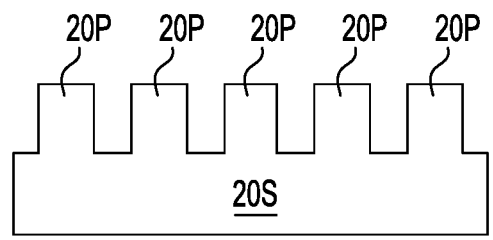
FIG. 7 is a cross sectional view of the exemplary structure of FIG. 6 after removing the mold from the electrode structure.

Referring now to FIG. 7, there is illustrated the exemplary structure of FIG. 6 after removing the mold 10S from the electrode structure (20S, 20P). In some embodiments of the present application, the mold 10S can be removed by completely dissolving the mold 10S utilizing a wet chemical etchant. In another embodiment, the mold 10S may be removed using reactive ion etching (RIE). In such embodiments, the mold 10S is a single-use mold.

In some embodiments, the mold 10S may be removed by slipping the resultant electrode structure (20S, 20P) from the mold 10S. In such an embodiment, the mold 10S may be reused multiple times. In such an instance, a release agent such as, for example, silicone, may be applied to the inside of the mold 10S prior to introducing the fill material 20 into the mold 10S. The release agent may include any chemical that can prevent bonding of the fill material to the exposed surfaces of mold 10S.

Figure 8:
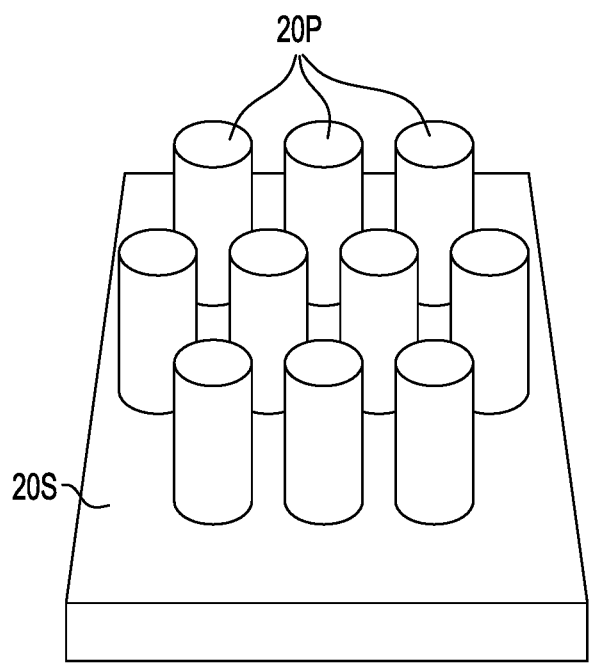
FIG. 8 is a three-dimensional representation of the electrode structure in accordance with an embodiment of the present application.

Referring now to FIG. 8, there is illustrated a three-dimensional representation of the electrode structure (20S, 20P) in accordance with an embodiment of the present application. In this embodiment, each non-random individual articulated feature 20P that provides the non-random topography of the electrode structure is in the shape of a nanorod that extends upward from the electrode base 20S. Additional corresponding wiring and/or associated probe pads required for interpretation of the electrical signal may also be included (not shown).

Figure 9:
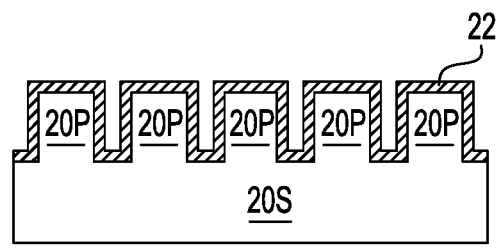
FIG. 9 is a cross sectional view of the exemplary structure of FIG. 7 after the attachment of a biological molecule to the surface of the electrode structure, which is also referred to as a functionalization process.

After forming the electrode structure shown in FIG. 7 or FIG. 8, in order to functionalize the structure to respond as a biosensor, a biological functionalized material 22 can be applied to the surface of the electrode structure (20S, 20P) as shown in FIG. 9, including each non-random individual articulated feature 20P that provides the nanotopography shape of the electrode structure of the present application. Any of the exposed areas of the electrode base 20S may also be coated with the biological functionalization material 22. The electrode structure (20S, 20P) can be used as a component in various biosensors which include other well-known components, such as but not limited to, reference and counter electrode structures.

By "biological functionalization material" it is meant any bioreceptor that binds with a complementary target biomolecule to create a binding event. In the primary embodiment, biochemical reactions involving the biological functionalization material generate an electrical signal which can be conducted by the non-random individual articulated feature 20P of the electrode structure of the present application under an applied electric potential. Examples of biological functionalization materials that can be used in the present application include an oligonucleotide, a nucleic acid, a peptide, a ligand, a protein, an enzyme, or any other material apt to bind with a complementary target biomolecule. When the electrode structure (20P, 20S) of the present application is used for glucose sensing, the biological functionalization material 22 can be composed of glucose oxidase or glucose dehydrogenase.

The biological functionalization material 22 can be applied to the electrode structure (20S, 20P) of the present application utilizing established biological functionalization processes known to those skilled in the art. Such biological functionalization processes typically include a series of chemical reactions that attach the biological functionalization material 22 on the surface of the electrode structure of the present application.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A method of forming an electrode structure, the method comprising:
providing a mold having a pattern that comprises both at least one first opening defining an electrode base shape and a second opening defining a nanotopography shape including a plurality of non-random individual articulated features, the first opening and second opening present entirely in the mold, wherein the second opening is directly connected to the first opening and the second opening has a critical dimension that is less than a critical dimension of the first opening;
introducing a metallic glass into the mold utilizing a thermoplastic forming process to provide an electrode structure comprising the metallic glass and having the electrode base substrate shape and the nanotopography shape of the mold;
removing the mold from the electrode structure; and
attaching a biological functionalization material to the electrode structure, wherein the biological functionalization material is a bioreceptor that binds with a complementary biomolecule to create a binding event that generates an electrical current that can be conducted by the electrode structure.

2. The method of claim 1, wherein the removing of the mold comprises:
contacting the mold with a chemical wet etchant.

3. The method of claim 1, wherein the bioreceptor is composed of an oligonucleotide, a nucleic acid, a peptide, a protein, or an enzyme.

4. The method of claim 1, wherein the providing the mold comprises:
first patterning a substrate to provide the electrode base shape in the substrate; and
second patterning the substrate containing the electrode base shape to provide the nanotopography shape into the substrate.

5. The method of claim 4, wherein the substrate is composed of a semiconductor material.

6. The method of claim 4, wherein the substrate is composed of a dielectric material.

7. The method of claim 4, wherein the substrate is composed of a ceramic material, an elemental metal or an alloy containing an elemental metal.

8. The method of claim 1, wherein the metallic glass is a solid metallic material or metal alloy with a disordered amorphous atomic structure.

9. The method of claim 1, wherein each non-random individual articulated feature has a shape of a rod, cone, ellipse or an annular structure.

10. The method of claim 1, wherein each non-random individual articulated feature has a pitch ratio from 2:1 to 100:1 and an aspect ratio from 1:1 to 500:1.

11. The method of claim 1, wherein the thermoplastic forming process comprises:
heating the metallic glass above a glass transition point of the metallic glass; and
applying an external compressive force to flow melted metallic glass into the mold.

12. The method of claim 11, wherein the thermoplastic forming process is performed in an inert ambient.

13. The method of claim 11, wherein the thermoplastic forming process is performed in air.

14. The method of claim 11, further comprising cooling the mold containing the melted metallic glass to room temperature.

15. The method of claim 1, further comprising removing, after performing the thermoplastic forming process, excess metallic glass that is located above the mold.

16. The method of claim 15, wherein the removing of the excess metallic glass comprises a planarization process, a chemical etch back process, or reactive ion etching.

17. The method of claim 1, wherein the metallic glass is composed of a PtCuNiP alloy.

18. A method of forming an electrode structure, the method comprising:
providing a mold having a pattern that comprises both an electrode base shape and a nanotopography shape;
introducing a metallic glass into the mold utilizing a thermoplastic forming process to provide an electrode structure comprising the metallic glass and having the electrode base substrate shape and the nanotopography shape of the mold;
removing the mold from the electrode structure; and
attaching glucose oxidase to the electrode structure.

19. A method of forming an electrode structure, the method comprising:
providing a mold having a pattern that comprises both an electrode base shape and a nanotopography shape;
introducing a metallic glass into the mold utilizing a thermoplastic forming process to provide an electrode structure comprising the metallic glass and having the electrode base substrate shape and the nanotopography shape of the mold;
removing the mold from the electrode structure; and
attaching glucose dehydrogenase to the electrode structure.

\* \* \* \* \*